United States Patent [19]

Schlicht

[11] Patent Number: 4,579,674
[45] Date of Patent: Apr. 1, 1986

[54] HYDROCARBYLSUCCINIMIDE OF A SECONDARY HYDROXYL-SUBSTITUTED POLYAMINE AND LUBRICATING OIL CONTAINING SAME

[75] Inventor: Raymond C. Schlicht, Fishkill, N.Y.

[73] Assignee: Texaco Inc., White Plains, N.Y.

[21] Appl. No.: 334,774

[22] Filed: Dec. 28, 1981

[51] Int. Cl.[4] ........................................... C10M 133/44
[52] U.S. Cl. ............................ 252/51.5 A; 548/545; 548/546
[58] Field of Search ................ 252/51.5 A; 548/545, 548/546

[56] References Cited

U.S. PATENT DOCUMENTS

| | | | |
|---|---|---|---|
| 3,017,362 | 1/1962 | Cyba | 252/51.5 A |
| 3,251,852 | 5/1966 | DeGroote et al. | 252/51.5 A X |
| 3,272,746 | 9/1966 | LeSuer et al. | 252/51.5 A X |
| 3,282,955 | 11/1966 | LeSuer | 252/51.5 A X |
| 3,373,111 | 3/1968 | LeSuer et al. | 252/51.5 A |
| 3,705,109 | 12/1972 | Hausler et al. | 252/51.5 A X |
| 3,813,228 | 5/1974 | Geiser | 252/51.5 A X |

Primary Examiner—Jacqueline V. Howard
Attorney, Agent, or Firm—Robert A. Kulason; James J. O'Loughlin

[57] ABSTRACT

A new hydrocarbyl-substituted succinimide of a secondary hydroxyl-substituted diamine or polyamine represented by the formula:

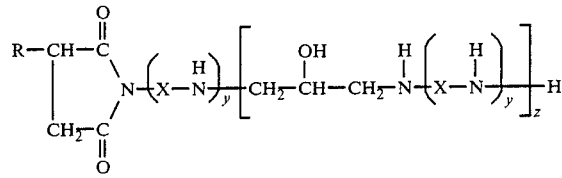

in which R is a hydrocarbon radical having from 50 to 400 carbon atoms, X is a divalent hydrocarbon radical having from 2 to 6 carbon atoms, and y and z are numbers from 1 to 10, a method of preparing same, and a lubricating oil composition are provided.

19 Claims, No Drawings

HYDROCARBYLSUCCINIMIDE OF A SECONDARY HYDROXYL-SUBSTITUTED POLYAMINE AND LUBRICATING OIL CONTAINING SAME

BACKGROUND OF THE INVENTION

1. Field of the Invention

Internal combustion engines operate under a wide range of temperatures including low-temperature stop-and-go service as well as high temperature conditions produced by continuous high speed driving. Stop-and-go driving, particularly during cold, damp weather conditions leads to the formation of a sludge in the crankcase and in the oil passages of a gasoline or a diesel engine. This sludge seriously limits the ability of the crankcase oil to lubricate the engine. In addition, the sludge with its entrapped water tends to contribute to rust formation in the engine. The noted problems tend to be compounded by standard lubrication service recommendations for extended oil drain intervals.

It is known to employ nitrogen-containing dispersants and/or detergents in the formulation of crankcase lubricating oil compositions. Many of the known dispersant/detergent compounds are based on the reaction of an alkenylsuccinic acid or anhydride with an amine or polyamine to produce an alkylsuccinimide or an alkenylsuccinamic acid as determined by selected conditions of reaction.

It is also known to chlorinate alkenylsuccinic acid or anhydride prior to the reaction with an amine or polyamine in order to produce a reaction product in which a portion of the amine or polyamine is attached directly to the alkenyl radical of the alkenylsuccinic acid or anhydride. The thrust of many of these processes is to produce a product having a relatively high level of nitrogen in order to provide dispersancy in a lubricating oil composition.

With the introduction of smaller internal combustion engines which must operate at high speeds to produce the required torque output, it has become increasingly difficult to provide a satisfactory dispersant lubricating oil composition.

Another problem facing the industry is that of lubricating small diesel engines which have become increasingly popular for powering passenger motor vehicles. Diesel or compression ignition engines put new levels of lubrication and dispersant requirements on the crankcase lubricant and these needs are not satisfactorily met by conventional motor oils.

It is an object of this invention to provide a novel lubricating oil additive.

Another object is to provide a method for preparing a novel lubricating oil composition.

A further object is to provide a lubricating oil composition having improved dispersant properties for spark ignited and compression ignited internal combustion engines.

2. Description of the Prior Art

U.S. Pat. No. 3,172,892 discloses an alkenylsuccinimide formed from the reaction of an alkenylsuccinic anhydride and an alkylene polyamine and its use as a dispersant in a lubricating oil composition.

Netherlands Pat. No. 7,509,289 discloses the reaction product of an alkenylsuccinic anhydride and an aminoalcohol, namely a tris(hydroxymethyl)-aminomethane.

SUMMARY OF THE INVENTION

The novel hydrocarbylsuccinimide of a secondary hydroxyl-substituted polyamine of the invention is represented by the formula:

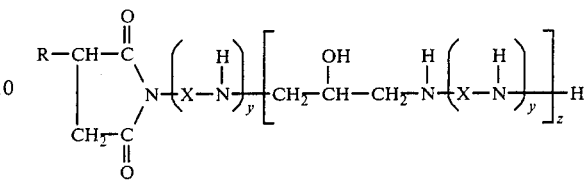

in which R is a hydrocarbon radical having from 50 to 400 carbon atoms, X is a divalent hydrocarbon radical having from 2 to 6 carbon atoms, and y and z are numbers from 1 to 10.

The prescribed succinimide is prepared by first reacting a diamine or polyamine with a glycidyl halide, such as epichlorohydrin, to form an intermediate compound characterized by having one or more secondary hydroxyl groups followed by the reaction of this intermediate compound with a hydrocarbyl-substituted succinic anhydride to form the prescribed hydrocarbylsuccinimide of a secondary hydroxyl-substituted diamine or polyamine of the invention.

The lubricating oil composition of the invention comprises a lubricating oil base and an effective dispersant amount of the prescribed hydrocarbylsuccinimide.

DESCRIPTION OF THE PREFERRED EMBODIMENTS

The hydrocarbylsuccinimide of a secondary hydroxyl-substituted diamine or polyamine of the invention is represented by the formula:

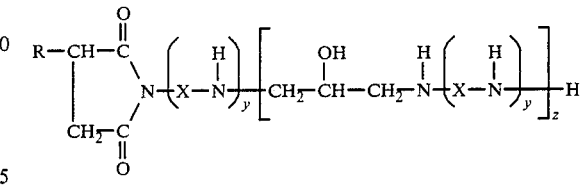

in which R is a monovalent hydrocarbon radical having from 50 to 400 carbon atoms, preferably 50 to 200 carbon atoms, X is a divalent hydrocarbon radical having from 2 to 6 carbon atoms, preferably 2 to 3 carbon atoms, and y and z are numbers from 1 to 10 and preferably numbers from 1 to 5.

A more preferred hydrocarbylsuccinimide of the invention is represented by the formula:

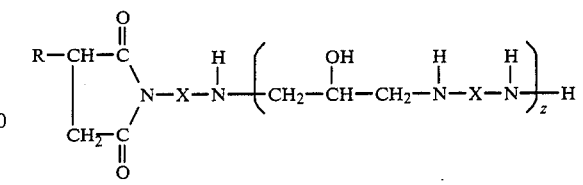

in which R is a monovalent hydrocarbon radical having from about 50 to 200 carbon atoms, X is a divalent hydrocarbon radical having from 2 to 3 carbon atoms, and z is a number from 1 to 3. Still more preferred are the compounds in which R is a hydrocarbyl radical having from about 50 to 100 carbon atoms and z is a number from 1 to 2.

An essential feature of the novel compound of the invention is the presence of at least one secondary hydroxyl group in the diamine or polyamine radical present in the prescribed hydrocarbyl-substituted succinimide compound of the invention. The structural unit with the secondary hydroxyl group imparts improved dispersancy properties and is critical to the performance of this class of compounds.

The prescribed secondary hydroxy hydrocarbyl-substituted succinimide of the invention is prepared in a two-step reaction. In general, a diamine or a polyamine having at least two primary amine groups, such as an alkylene polyamine, is reacted with a glycidyl halide, such as epichlorohydrin to form an intermediate secondary hydroxy-substituted diamine and analogous polyamine compounds. Generally, two or more moles of the diamine or polyamine are reacted with each mole of glycidyl halide. The reaction may be conducted employing from 2 to 5 moles of the diamine or polyamine for each mole of epichlorohydrin with the preferred ratio being from about 2 to 3 moles of the diamine or polyamine. The intermediate product produced by this reaction is characterized by having one or more of the secondary hydroxy radical. Such a reaction between ethylenediamine and epichlorohydrin is illustrated in the following equation:

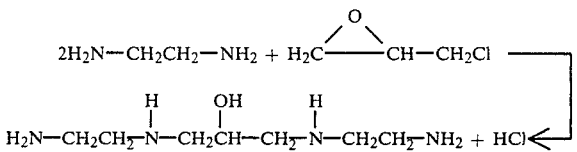

The formation of polyamines is exemplified by the further reaction of the above amine, N,N'-bis-2-aminoethyl-1,3-diaminopropan-2-ol, with epichlorohydrin and ethylenediamine in similar fashion. The resultant product mixture is composed of components having the general structure,

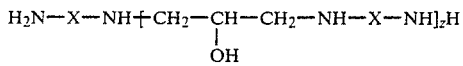

where X and z have the precedingly described values. Some branched chain products may also be produced.

The diamine or polyamine which can be employed to react with the glycidyl halide is represented by the formula:

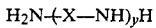

in which X is a divalent hydrocarbon radical having from 2 to 6 carbon atoms, preferably 2 to 3 carbon atoms, and y is a number from 1 to 10, preferably from 1 to 5, and still more preferably 1 to 3. Typical diamines and polyamines which can be employed for preparing the intermediate reaction product include ethylenediamine, diethylenetriamine, triethylene tetramine, tetraethylene pentamine, pentaethylene hexamine, 1,3-propanediamine, 1,4-butanediamine, 1,6-hexanediamine or a mixture thereof.

The glycidyl halide may be epichlorohydrin, epibromohydrin, epiiodohydrin, and epifluorohydrin, and it may also bear other non-interfering substituents, such as alkyl, aryl, halogen, nitrile, alkoxy and aryloxy groups.

This reaction is conducted at a temperature ranging from about 0° to 200° C. The preferred reaction temperature, however, is in the range of 20° to 100° C.

A base is employed to convert the amine hydrochloride to its free base. Suitable bases include an alkali or alkaline earth hydroxide, oxide, carbonate, silicate, aluminosilicate or other salt of a weak acid, ammonia or an organic base.

The secondary hydroxy-substituted diamine or polyamine described above is reacted with a hydrocarbyl-substituted or a halogenated hydrocarbyl-substituted succinic anhydride or its corresponding succinic acid in the second step of the preparation. The anhydride reactant is represented by the formula:

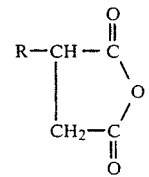

in which R is a hydrocarbyl or monovalent hydrocarbon, or frequently alkenyl radical or a halogenated hydrocarbyl radical having from about 50 to 400 carbon atoms, preferably from 50 to 200 carbon atoms. A more preferred reactant is an alkenylsuccinic anhydride in which the alkenyl radical has from about 60 to 100 carbon atoms.

The noted hydrocarbyl-substituted succinic anhydride is reacted with the prescribed secondary hydroxy-substituted amine or polyamine using approximately a 0.5:1 to 1:1 mole ratio and reaction conditions selected to produce a conventional succinimide reaction. The amine chain from the secondary hydroxy-substituted diamine or polyamine in the succinimide product is unchanged in this reaction and continues to be characterized by having a structural unit with a secondary hydroxyl group which is responsible for the unique properties to these new compounds.

The following examples illustrate the preparation of the intermediate secondary hydroxy-substituted diamine/or polyamine mixture.

EXAMPLE I

Preparation of an Amine from Ethylenediamine And Epichlorohydrin with NaOH Initially Absent A 462.5 g. (5.0 mole) quantity of epichlorohydrin was added to 900 g. (15.0 mole) of ethylenediamine while allowing the temperature to rise to a maximum of 80° (cooling as necessary). Upon completion of the addition, the mixture was stirred 3 hours at 80° and then for 1 hour at 100°. After cooling to 40° C., vacuum was applied to the flask and unreacted ethylenediamine was removed by distillation to 80° at about 10 mm Hg pressure. The residue was cooled to about 70° and then 84.0 g. (1.05 mole) of a 50% aqueous NaOH solution was stirred in. This mixture was cooled to 40° (while stirring) and again distilled at 10 mm. pressure up to 80° C., removing water and residual ethylenediamine. Then 200 ml isopropanol was stirred in and the mixture cooled to room temperature. Next, the mixture was filtered to remove the by-product NaCl. The filtrate was then distilled to 80° at about 10 mm., removing the alcohol and recovering the product as the distillation residue. The yield was 721 g. The analyses were 27.01% N, 0.45% Na, and 0.16% Cl.

IR and Spectral Data

Amine of Example I Process

The attached 1H and 13C NMR spectra for this example demonstrate that the amine product possesses the indicated functionalities.

| NMR | 1H | | 13C | |
|---|---|---|---|---|
| Functional Group | Found | Expected | Found | Expected |
| Chemical Shift, ppm | | | | |
| sec CH—OH | 3.7–3.9, m | (3.8) | 71 | (52–81) |
| —CH$_2$N, | 2.5–3.0, m | (2.5) | 43,53.5,55 | (38–60) |
| NH, | 2.3, s | variable | — | |
| CH$_2$OH reference | — | (3.55) | — | (40–70) |

[1] Silverstein and Bassler, "Spectrophotometric Identification of Organic Compounds" Wiley, 1961
[2] Wehrli and Wirthlin, "Interpretation of carbon-13 NMR Spectra", Heyden and Sons, 1976.
[3] Dolphin and Wick, "Tabulation of Infrared Spectral Data", John Wiley and Sons, 1977.

EXAMPLE 2

Amine Prepared by Reaction of 1,3-Propanediamine (PDA) and Epichlorohydrin

Substituting 1,3-propanediamine for ethylenediamine, the procedure of the preceding example was employed to prepare an amine mixture of the generic structure on p. 5 where X=—CH$_2$CH$_2$CH$_2$—.

The materials used were as follows:

| 1,3-Propanediamine | 444 g. | (6.0 moles) |
|---|---|---|
| Epichlorohydrin | 185 g. | (2.0 moles) |
| NaOH as 50% aq. conc. | 168 g. | (2.1 moles) |
| Isopropanol | 660 ml. | — |

The yield of product was 334 g. The analyses obtained were as follows:

| | Found | Calculated |
|---|---|---|
| % N | 23.3; 23.7 | 27.4 |
| % Na | 0.33 | 0 |
| % Cl | 0.029 | 0 |

The IR and NMR analyses were similar to those of the ethylenediamine products.

EXAMPLE 3

Preparation of a n-Tetradecenylsuccinimide of an Ethylenediamine:Epichlorohydrin Amine An 88.20 g. (0.3 mole) quantity of distilled n-tetradecenylsuccinic acid anhydride (Humphrey Chemical Company) was added to a stirred mixture of 47.52 g. (0.27 mole) of the amine (at 27.0% N=0.92 Eq. of Example 1 and 200 ml. xylene. The mixture was heated to reflux under an N$_2$ atmosphere, collecting the water of reaction (6.6 ml) in a Dean-Stark trap over a 5 hr. period. The reaction mixture was then cooled to room temperature and filtered through diatomaceous earth. The filtrate was then distilled to remove solvent up to 130° C. at 10 mm. Hg. pressure recovering the product as 123.5 g. of distillation residue. The analyses of the product found were as follows (calculated values in parenthesis): %N=10.34 (9.85), Total Acid Number=4.8 (0), Total Base Number=243 (266).

Further, the product was subjected to infrared and NMR analysis with the following results:

| IR Spectrum | cm$^{-1}$ | Functional Group |
|---|---|---|
| | 3600–3800 | OH (shoulder on next peak) |
| | 3310 | NH |
| | 1760 | succinimide C=O |
| | 1690 | |

$^{13}$C-NMR Spectrum

The $^{13}$C-NMR spectrum of Ex. 3 is shown without (usual procedure) and with "off-resonance decoupling". The former eliminates the effect of H atoms on the C spectrum, while the "off-resonance decoupling" permits the determination of the number of H atoms directly bonded to a C atom.

The upper spectrum shows a peak at 69 ppm, corresponding to the CHOH group as shown previously for the amine intermediate (at 71 ppm). The lower spectrum shows the 69 ppm peak to be split into a doublet; this behavior is to be expected for a secondary alcohol function with only one C—H bond. A primary alcohol would provide a triplet because two CH bonds are present.

EXAMPLE 4

Preparation of an Amine from Ethylenediamine And Epichlorohydrin with NaOH Present Initially A reaction flask is charged with 900 g (15.0 mole) ethylenediamine and 210 g. (5.25 mole) sodium hydroxide. Then 462.5 g. (5.0 mole) epichlorohydrin is added gradually over 1–1.5 hr. at 30°–40°, cooling as necessary to control the exotherm. The mixture is stirred 1 hr. at 30°–40° until the exotherm is diminished, and then it is heated to 80°, at which it is stirred for 3 hrs. The mixture is then heated to 100° and stirred another hour to complete the reaction. After cooling the mixture to less than 50° C., the pressure is reduced while distilling off an overhead of water and unreacted ethylenediamine. The temperature is raised to 80° C. while reducing the pressure to about 10 mm Hg to essentially complete the removal of distillate. After 1 hr. at 80° and 10 mm Hg pressure, the pressure is raised to atmospheric, and about 700 ml. isopropyl alcohol is stirred in while cooling to room temperature. The mixture is then filtered, using 700 ml. more alcohol to complete the washing of the product into the filter flask. The filtrate is then stripped to 80° C. max., reducing the pressure to 10 mm Hg. The recovery of product (pot residue) was 735 g. (147 g/mole epichlorohydrin). The analyses on the product are as follows:

| | Found | Calculated |
|---|---|---|
| % N | 27.8 | 31.8 |
| % Na | 0.30 | 0 |
| % Cl | 0.13 | 0 |

Infrared and NMR($^1$H and $^{13}$C) analyses conform the presence of N,N'-bis-2-aminoethyl-1,3-diaminopropan-2-ol represented by the formula:

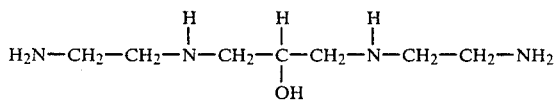

EXAMPLES 5-7

Examples of the preparation of amines from ethylenediamine and epichlorohydrin, by the Example 4 procedure but for employing other charge ratios, are provided in the following stable. The materials charged were in the indicated proportions and reaction scale.

TABLE I
PREPARATION OF AMINES, USING VARIOUS CHARGE RATIOS OF ETHYLENEDIAMINE AND EPICHLOROHYDRIN

| Ex. No. | 5 | 6 | 7 |
|---|---|---|---|
| Charge Ratio of Ethylene:Epichlorohydrin (molar) | 6:1 | 2:1 | 1.25:1 |
| Reaction Scale (moles epichlorohydrin) | 0.6 | 1.0 | 1.0 |
| Yield of Product, g/mole Epichlorohydrin) | 161 | 131 | 117 |
| Analyses | | | |
| % N | 27.9 | 23.9 | 23.0 |
| % Na | 0.20 | 0.21 | 0.01 |
| % Cl | 0.15 | 0.29 | 0.17 |

The foregoing results show that both the yields of product and nitrogen content decrease as the charge ratio of ethylenediamine:epichlorohydrin decreases from 6:1 to 1.25:1.

EXAMPLE 8

Amine Prepared by Reaction at 60°-80° of Ethylenediamine:Epichlorohydrin (3:1 Mole Ratio Charged)

A mixture of 108.0 g (1.80 mole) ethylenediamine and 25.20 g (0.63 mole) sodium hydroxide was heated with stirring to 60° before adding 55.50 g (0.60 mole) epichlorohydrin over 1 hr. at 60°-80° (cooling as necessary after the initial exotherm to 80° C.). The final mixture was stirred 3 hrs. at 80° and 1 hr. at 100°, and then worked up as in Example 4. The yield of product was 83.8 g (140 g/mole epichlorohydrin), which gave the following analyses: % N=27.7, % Na=0.42, % Cl=0.35. Since these results indicate that this product is comparable to the Example 4 product, the temperature used to combine the ethylenediamine and epichlorohydrin is not critical over the 60°-80° C. range.

EXAMPLE 9

Preparation of an Amine, Charging Ethylenediamine and Epichlorohydrin in 4:1 Mole Ratio, with Benzene Added Later to Remove the Water and Unreacted Ethylenediamine by Azeotropic Distillation A 46.27 g (0.5 mole) quantity of epichlorohydrin was charged to a mixture of 120.0 g. (2.0 mole) ethylenediamine, and 20.00 g (0.5 mole) sodium hydroxide, over 15 minutes at 30°-35°, at which temperature it was stirred (with further cooling) for 1 hr. The mixture was heated to 100° and stirred another hour. Then, after cooling the mixture to 80° C., 150 ml of benzene was added, and the mixture was heated to reflux. After 2½ hrs. reflux, 25 ml. of aqueous ethylenediamine distillate had been collected by use of a Dean-Stark trap. The two-phase pot residue was filtered and stripped to 80° at 175 mm Hg pressure. The yield was 80 g with these analyses: % N=30.2, % Na=0.13, % Cl=0.75.

EXAMPLE 10

Preparation of an Amine from Ethylenediamine and Epichlorohydrin in the Presence of Ethylene Glycol Dimethylether A mixture of 360 g. (6.0 mole) ethylenediamine, 80.0 g. (2.0 mole) NaOH, and 50 ml. ethylene glycol dimethylether was stirred while adding 185.0 g (2.0 mole) epichlorohydrin at 20°-35° over 1.5 hr. with cooling. The temperature was then heated to 80°, at which it was stirred 1 hr. The mixture was then cooled slightly and 200 ml cyclohexane was added. The mixture was then refluxed 4 hrs. at 75°-7°, collecting 102 ml. of aqueous ethylenediamine distillate. The two-phase mixture was cooled to room temperature and filtered, washing the viscous amine phase through the filter with isopropyl alcohol. The combined filtrate was stripped to 80° at 0.5 mm Hg pressure, obtaining 276 Hg of product. The analytical results were % N=27.3, 27.2; Na=0.48; % Cl=1.09.

EXAMPLE 11

Preparation of an Amine, Charging Ethylenediamine and Epichlorohydrin in 3:1 Mole Ratio, by the Example 10 Procedure But in the Absence of Polar Solvent Using a 5% Excess of NaOH The Example 10 procedure was employed with the following materials charged: 900 g (15.0 mole) ethylenediamine, 462.5 g (5.0 mole) epichlorohydrin, 210 g. (5.25 mole) NaOH, and 300 ml. cyclohexane. Also the ethylenediamine, epichlorohydrin, NaOH reaction mixture was stirred for 3 hrs. at 80° before adding the cyclohexane. This mixture was refluxed 14 hrs. at 80° max, removing 486 ml. of aqueous ethylenediamine by azeotropic distillation. Then 500 ml isopropanol was added and the mixture filtered at room temperature. Final stripping yielded 704 g. product which analyzed as follows: % N=28.29, % Na=0.22, % Cl=0.10. The use of a 5% excess of NaOH provided a reduced Cl content as desired.

The use of amines other than ethylenediamine in the preparation of amine:epichlorohydrin reaction products is demonstrated in the following examples.

EXAMPLE 12

Preparation of a Diethylenediamine:Epichlorohydrin Reaction Product (3:1 Mole Ratio in Charge)

A mixture of 185.4 g (1.8 mole) diethylenetriamine (DETA) and 25.2 g (0.63 mole) sodium hydroxide was stirred while adding 55.5 g (0.60 mole) epichlorohydrin at 30°-40° over 1 hr., and this mixture was stirred 1 hr at 38°-40°. Then the mixture was heated to 80° and stirred 3 hrs., followed by 1 hr. at 100°. The Example 4 work-up procedure was followed, except the product was finally stripped at 100°/1 mm Hg pressure to complete the removal of unreacted DETA. The yield was 120.5 g (201 g/mole epichlorohydrin). The analyses were 29.0, 29.2% N; 0.165% Na; and 0.11% Cl (theoretical values were 32.06% N and 0% for Na and Cl.

(1) Calculated for the desired product:

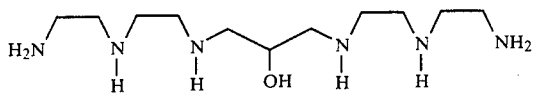

EXAMPLE 13

Preparation of an Amine:Epichlorohydrin Reaction Product, Employing Stepwise Reaction of Two Different Amines (Diethanolamine and Ethylenediamine)

A 105.0 g (1.0 mole) quantity of diethanolamine (di-2-hydroxyethylamine) was stirred with cooling at 10°–30° while adding 92.50 g (1.0 mole) epichlorohydrin over 2 hrs. After stirring 2 hrs. at 25°–30° and then standing overnight, 42.0 g (1.05 mole) NaOH was added, followed by 120 g (2.0 mole) ethylenediamine over 1 hr at 30°–40°. After 1 hr. further stirring at 30°–40°, the mixture was heated to 80° and stirred 1 hr. The mixture was worked up as in Example 4, obtaining 207.9 g. of final product.

The analyses were as follows:

|      | Found | Calculated[1] |
|------|-------|---------------|
| % N  | 15.5  | 19.0          |
| % Na | 1.01  | 0             |
| % Cl | 1.19  | 0             |

[1]Calculated for (HO⁀)₂N⁀N⁀NH₂ with OH and H substituents

The nitrogen analysis indicates that the product was a mixture of the desired mixed reaction product and product(s) derived from diethanolamine only.

The following examples illustrate the preparation of the secondary hydroxy hydrocarbyl-substituted succinimide of the invention from the secondary hydroxy-substituted diamines and polyamines described hereinabove. In all of these examples the moles of amine indicated were calculated on the basis of the theoretical product (2 moles reactant amine:epichlorphydrin).

EXAMPLE 14

Preparation of a Polybutenylsuccinimide of an Ethylenediamine:Epichlorohydrin amine with an Aromatic Hydrocarbon As Reaction Solvent A solution of 2116 g (1.0 mole)[1] polybutenylsuccinic acid anhydride (PBSA prepared from an approximately 1300 mol. wt. polybutene) in 1004 g. of a diluent oil (a paraffin distillate oil having a viscosity at 100° F. of about 100 Saybolt seconds) was added to a mixture of 158 g. of the amine of Example 10 (at 27.3% N=3.1 Eq. N), 1000 g. of the same diluent oil, and 200 ml xylene, the temperature rising from room temperature to about 60°. Then another 450 ml xylene was added, and the mixture was heated to reflux. After 3 hrs. at 180° max. during which 25.5 ml water was collected in a Dean-Stark trap, the pressure was reduced while stripping off solvent at 180° to about 10 mm Hg pressure. The yield was 4179 g. of an approximately 50% concentrate which contained 0.99, 1.00% N.

(1) The moles of dibasic acid anhydride is calculated from the Saponification Number determined for this batch of PBSA.

EXAMPLE 15

Preparation of a Polybutenylsuccinimide of an Ethylenediamine:Epichlorohydrin Amine in the Presence of a Mineral Oil as Reaction Medium and Product Diluent A mixture of 31.60 g of ethylenediamine:epichlorohydrin amine, prepared in the same manner as in Example 4, (at 27.9% N,=0.62 Eq. of nitrogen) and 401 g. of diluent oil (as used in Example 14) is stirred while 423 g. (0.20 mole) PBSA (same PBSA as in Example XI) is added over ½ hr. at 28°–73° (rise due to exotherm). The mixture is then heated under a N₂ stream to 160° where it is held for 2 hrs., thus distilling out the water of reaction. Then the hot mixture is filtered through diatomaceous earth filter aid. The product (an approximately 50% oil concentrate) analyzed as follows: % N=1.01 (1.02 calc). Total Acid Number (TAN)=0.9, and Total Base Number (TBN)=26.6.

EXAMPLE 16

Preparation of a Polybutenylsuccinimide of an Ethylenediamine:Epichlorohydrin Amine (Example 11 Product) by the Example 15 Reaction The amine product in Example 11 was used in reaction with the PBSA (prepared from 1300 vol. wt. polybutene) in the presence of the diluent oil, preparing approximately 5 gallons of the oil concentrate of the polybutenylsuccinimide. The product analysed as follows:

| % N                | 0.98          |
|--------------------|---------------|
| TAN                | 1.05          |
| TBN                | 21.7          |
| Sp. Gr. 60/60° F.  | 0.9169        |
| Color, ASTM Dilute | Less than 3.0 |
| % Water (Karl-Fischer) | 0.083     |

Table II (following) provides examples of preparations of polybutenylsuccinimides of (a) amines prepared using various ratios of ethylenediamine and epichlorohydrin (as in Examples 4, 5, 6 and 7), (b) by use of different ratios of PBSA to amine, and (c) by use of the Example 1 procedure.

TABLE II

POLYBUTENYLSUCCINIMIDES OF VARIOUS AMINE PREPARATIONS

| Succinimide No. | Amine Reactant EDA:ECH Ratio | Ex. No. | Polybutenylsuccinimide Reactant Ratio Eq. N:Mole ASAA | Analyses % N | Ex. TBN |
|---|---|---|---|---|---|
| (a) Ethylenediamine:Epichlorohydrin Amines | | | | | |
| 17 | 6:1    | 5     | 3.1  | 0.90 | 23.9 |
| 16 | 3:1    | 11    | 3.1  | 0.98 | 21.7 |
| 18 | 2:1    | 6     | 3.1  | 1.09 | 19.7 |
| 19 | 1.25:1 | 7     | 4.0  | 1.11 | 28.4 |
| 20 | 3:1    | (=4)  | 2.0  | 0.74 | 26.7 |
| 21 | 3:1    | (=4)  | 3.5  | 0.95 | 35.2 |
| 22 | 2:1    | 7     | 2.0  | 0.70 | 9.5  |
| 23 | 3:1    | 1     | 3.05 | 0.99 | 25.3 |
| (b) Other Amine:Epichlorohydrin Preparations Amine(s) | | | | | |
| 24 | DETA    | 12 | 4.0 | 1.68 | 38.5 |
| 25 | DEA:EDA | 13 | 2.2 | 0.68 | 18.5 |
| 26 | 1,3-PDA | 2  | 3.1 | 1.02 | 29.1 |

The lubricant composition of the invention comprises a major amount of a mineral, hydrocarbon oil or synthetic oil of lubricating viscosity and an effective detergent-dispersant amount of the prescribed secondary hydroxy hydrocarbyl-substituted succinimide. Advantageously, in the finished lubricating oil composition, the prescribed detergent-dispersant content will range between about 0.1 and 10 percent by weight, preferably between about 0.5 and 5 weight percent. In lubricating oil concentrates, from which the finished lubricating compositions are derived via the addition of added lubricating oil, secondary hydroxy hydrocarbyl-succinimide contents between about 10 and 90 weight percent are found.

The hydrocarbon oil in the finished lubricating composition advantageously constitutes at least about 80 weight percent and preferably between about 85 and 98 weight percent of the composition, and in the lube oil concentrates between about 50 and 90 weight percent of the composition. It is to be noted that even in the lubricating oil concentrates, the prescribed secondary hydroxy hydrocarbyl-substituted succinimide will exhibit effective detergent-dispersancy properties.

Examples of the hydrocarbon base oil contemplated herein are the naphthenic base, paraffinic base and mixed base mineral oils, lubricating oils derived from coal products and synthetic oils, e.g., alkylene polymers such as polypropylene and polyisobutylene of a molecular weight of between about 250 and 2500. Advantageously, a lubricating base oil having a lubricating oil viscosity at 100° F. of between about 50 and 1000, preferably between about 100 and 600, are normally employed for the lubricant compositions and concentrates thereof. (SUS basis)

In the contemplated finished lubricating oil compositions other additives may be included in addition to the dispersant of the invention. The additives may be any of the suitable standard pour depressants, viscosity index improvers, anti-wear agents, friction modifiers, oxidation and corrosion inhibitors, anti-foamants, supplementary detergent-dispersants, etc. The choice of the particular additional additives to be included in the finished oils and the particular amount thereof will depend on the use and conditions desired for the finished oil product.

The lubricating oil composition of the invention containing the prescribed secondary hydroxy hydrocarbyl-substituted succinimide was tested in a 10W-40 grade motor oil formulation. The Bench VC Dispersancy Test (BVCT), evaluates the ability of these additives to disperse sludge and varnish precursors generated on heating nitro-oxidized fuel components in the presence of the oil. A result of 10 or less in the BVCT indicates (on the basis of BVCT/Seq VC correlation studies) that the dispersant candidate has an excellent chance of performing satisfactorily in a full-scale engine test. The results in Table III show that all of the polybutenylsuccinimide preparations were effective dispersants in the BVCT, and gave blends which were low in color (where tested) and satisfactorily clear (Lumetron Turbidity values less than 12). The one exception in clarity was the blend of Example 24 which was prepared from an amine intermediate prepared from two different amine reactants.

TABLE III

BENCH VC, ASTM COLOR AND LUMETRON TURBIDITY TEST RESULTS ON OIL COMPOSITION

| Polybutenylsuccinimide Ex. No. | Test on Oil Blend[1] (at 8% Wt. of Dispersant) | | |
|---|---|---|---|
| | Bench VC Test | ASTM Color | Lumetron Turbidity |
| (a) Ethylenediamine:Epichlorohydrin Amines | | | |
| 17 | 6.0 | — | 5.0 |
| 16 | 3.0 | 2.5 | 7.0 |
| 18 | 7.5 | 3.0 | 3.0 |
| 19 | 5.5 | 3.0 | 3.0 |
| 20 | 9.0 | — | 10.0 |
| 21 | 7.0 | — | 4.5 |
| 22 | 8.5 | — | 2.0 |
| 23 | 5.5 | — | 2.0[a] |
| (b) Other Amine:Epichlorohydrin Preparations | | | |
| 24 | 9.5 | 3.0 | 2.5 |
| 25 | 8.5 | 3.0 | 29.5 |
| 26 | 8.5[a] | — | 1.5[a] |

[1]Blended into a 10W-10 grade motor oil formulation also containing .23% Ca/o-verbased calcium sulfonate + 0.15% Zn/Zn dialkyldithiophosphate + 0.25% ashless antioxidant + 0.5% pour point depressant + 10% of an oil concentrate of a VI improver in a base oil (SNO-7).
[a]This additive was blended at 6.5% wt.

As further evidence of the utility of the subject polybutenylsuccinimides as dispersants in lubricating oil formulations, bench and engine test results are shown in Table IV for gasoline and diesel engine oil formulations containing the Example 14 and 16 preparations as dispersants. These data compare the subject dispersant preparations to a commercial polybutenylsuccinimide of triethylenetetramine which differs structurally from the subject compositions (see structure 2, page 4) only in lacking the —CHOH— group in the amine moiety where $X=2$ and $z=1$. The engine test data show the subject dispersant composition is distinguished from the commercial dispersant by being unusually effective as a diesel engine dispersant while still retaining excellent gasoline engine dispersancy. The excellent diesel performance is evidenced even at low dosages of the dispersant. The other tests show no detrimental effects with regard to rusting, bearing corrosion, or oxidative thickening.

TABLE IV

BENCH AND ENGINE TESTS ON OILS CONTAINING SUBJECT DISPERSANTS

| | Motor Oil Type | | | | |
|---|---|---|---|---|---|
| | SAE 15W-40 Commercial Oil | | SAE 10W-30 | SAE-30 | |
| Dispersant Additive | Ex. 14 | Commercial Dispersant[2] | Ex. 16 | Ex. 16 | Commercial Dispersant[2] |
| % Wt. (% N) | 5.0 (.05) | 5.5 (.05) | 3.0 (.03) | 6.5 (.065) | 6.5 (.065) |
| Remaining Composition | 1 | 1 | 3 | 4 | 4 |
| Cat 1 G-2 Test (CD limits) | | | | — | — |
| 120 hrs, % TGF | 49 | 67 | 51 | | |
| TWD | 146 | 143 | 212.5 | | |
| 480 hrs, % TGF (80 Max) | 57 | 82 | 62 | | |
| TWD (300 Max) | 245 | 322 | 292.5 | | |
| Seq. IID Test (SF Limits) | | | 8.86 | | |
| Average Engine Rust (8.5 min) | | | | | |
| PV-1 Test[5] (SF Limits for Seq. VD) | | | | | |
| Avg. sludge (9.4 min) | | | | 9.25 | 9.2 |
| Piston Skirt varnish (6.6 min) | | | | 6.81 | 7.2 |

TABLE IV-continued
BENCH AND ENGINE TESTS ON OILS CONTAINING SUBJECT DISPERSANTS

| | Motor Oil Type | | | | |
|---|---|---|---|---|---|
| | SAE 15W-40 Commercial Oil | | SAE 10W-30 | SAE-30 | |
| Dispersant Additive | Ex. 14 | Commercial Dispersant[2] | Ex. 16 | Ex. 16 | Commercial Dispersant[2] |
| Avg. engine varnish (6.6 min) | | | | 6.90 | 6.9 |
| Bench L-38 mg | | | | 26.6 | — |
| (good/poor ref. oils) | | | | (25.5/129.4) | |
| Bench IIID-2 | | | | | |
| 72 hr/% vis. incr. | | | | 119.5 | — |
| (good ref. oil) | | | | (230.4) | |

[1] Oil also contains .12% Zn/Zn dialkyldithiophosphates (ZDTP) + 2.6% wt. overbased calcium sulfonate + 1.32% wt. sulfurized calcium alkylphenolate + 0.25% wt. diarylamine + 0.25% wt. ashless rust inhibitor + 0.5% pour point depressant + 8.00% VI improver (15% act.) + 150 ppm antifoamant in a paraffinic base oil.
[2] A polybutenylsuccinimide of triethylenetetramine from approximately 1300 mol. wt. polybutene.
[3] Oil also contains 0.12% Zn/ZDTP + 1.29% wt. overbased Ca sulfonate + 1.32% sulfurized Ca alkylphenolate + 1.0% ashless friction modifier + 0.25% diarylamine + 0.25% ashless rust inhibitor + 0.05% pour depressant + 6.75% dispersant VI improver (15% act.) + 150 ppm anti-foamant in paraffin base oil.
[4] Oil also contains 0.15% Zn/ZDTP + 1.64% wt. overbased calcium sulfonate + 0.25% diarylamine + 0.15% ashless rust inhibitor + 0.05% pour point depressant + 150 ppm anti-foamant in a paraffin base oil.
[5] Preliminary test procedure which, with minor modification, was adopted as the Seq. VD Test.

The foregoing tests demonstrate that the hydrocarbylsuccinimide of a secondary hydroxyl-substituted polyamine of the invention are excellent dispersants for lubricating oil compositions and are surprisingly effective in both spark-ignited and compression-ignited internal combustion engines.

I claim:

1. A novel compound represented by the formula:

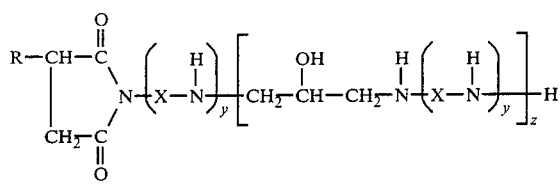

in which R is a hydrocarbon or a halogenated hydrocarbyl radical having from 50 to 400 carbon atoms, X is a divalent hydrocarbon radical having from 2 to 6 carbon atoms, and y and z are numbers from 1 to 10.

2. A novel compound represented by the formula:

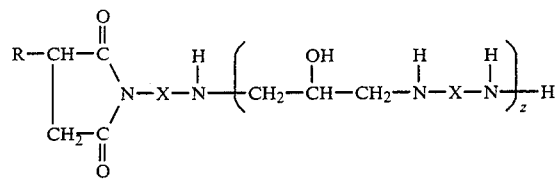

in which R is a monovalent hydrocarbon radical having from 50 to 200 carbon atoms, X is a divalent hydrocarbon radical having from 2 to 3 carbon atoms and z is a number from 1 to 3.

3. A compound according to claim 2 in which z is a number from 1 to 2.

4. A novel compound represented by the formula:

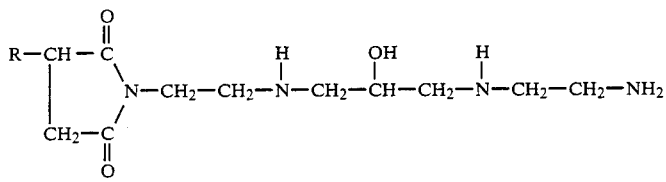

in which R is a hydrocarbon radical having from 50 to 200 carbon atoms.

5. A compound according to claim 4 in which R is a monovalent hydrocarbon radical having from about 60 to 100 carbon atoms.

6. A lubricant composition comprising a major proportion of an oil of lubricating viscosity and a minor dispersant amount of a compound corresponding to the formula:

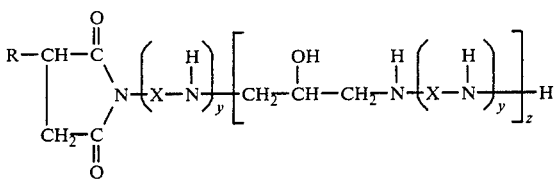

in which R is a hydrocarbon radical or a halogenated hydrocarbyl radical having from 50 to 400 carbon atoms, X is a divalent hydrocarbon radical having from 2 to 6 carbon atoms, and y and z are numbers from 1 to 10.

7. A lubricant composition comprising a major proportion of an oil of lubricating viscosity and a minor dispersant amount of a compound represented by the formula:

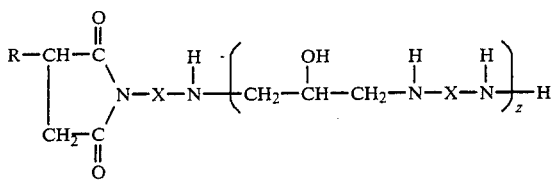

in which R is a monovalent hydrocarbon radical having from 50 to 200 carbon atoms, X is a divalent hydrocarbon radical having from 2 to 3 carbon atoms and z is a number from 1 to 3.

8. A lubricating oil composition according to claim 6 in which said dispersant compound is represented by the formula:

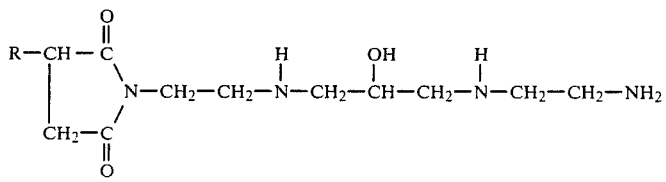

in which R is a hydrocarbon radical having from 50 to 200 carbon atoms.

9. A lubricating oil composition according to claim 8 in which R is a monovalent hydrocarbon radical having from about 60 to 100 carbon atoms.

10. A lubricant composition according to claim 6 containing from about 0.5 to 10 weight percent of said dispersant.

11. A lubricant composition according to claim 8 containing from about 0.5 to 10 weight percent of said dispersant.

12. A lubricating oil concentrate containing from about 10 to 65 weight percent of a compound represented by the formula:

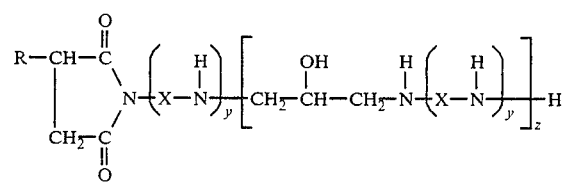

in which R is a hydrocarbon radical having from 50 to 400 carbon atoms, X is a divalent hydrocarbon radical having from 2 to 6 carbon atoms, and y and z are numbers from 1 to 10.

13. A lubricating oil concentrate according to claim 12 in which said compound is represented by the formula:

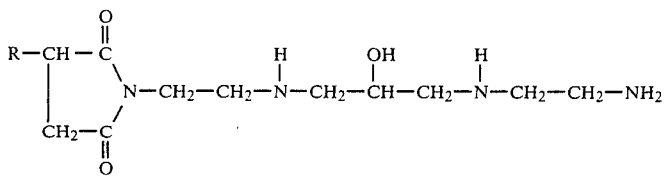

in which R is a hydrocarbon radical having from 50 to 200 carbon atoms.

14. A method for preparing a hydrocarbylsuccinimide having a seconary hydroxyl-substituted diamine or polyamine moiety which comprises reacting in the presence of a base a glycidyl halide having from 3 to 10 carbon atoms with an amine having at least two primary amine groups employing at least two moles of said amine per mole of said glycidyl halide to produce a polyamine reaction product characterized by having a secondary hydroxyl group and reacting said reaction product with a hydrocarbyl succinic anhydride, in which the hydrocarbyl radical has from about 50 to 400 carbon atoms to produce a hydrocarbylsuccinimide of a secondary hydroxyl-substituted diamine or polyamine.

15. The method of claim 14 wherein said hydrocarbyl radical as from about 60 to 100 carbon atoms.

16. A hydrocarbylsuccinimide prepared by the method of claim 14.

17. A lubricant composition comprising a major proportion of an oil of lubricating viscosity and a minor dispersant amount of the hydrocarbylsuccinimide of claim 16.

18. The lubricant composition of claim 17 containing from about 0.5 to 10 weight percent of said dispersant.

19. A concentrate composition comprising a minor proportion of an oil of lubricating viscosity and a major dispersant amount of the hydrocarbylsuccinimide of claim 16.

* * * * *